(12) United States Patent
Olson et al.

(10) Patent No.: US 8,313,920 B2
(45) Date of Patent: Nov. 20, 2012

(54) HIGH-THROUGHPUT ASSAY FOR EVALUATING DIPEPTIDYL PEPTIDASE I ACTIVITY

(75) Inventors: Matthew Olson, Spring City, PA (US); Matthew Todd, Downingtown, PA (US)

(73) Assignee: Janssen Research & Development, LLC, Raritan, NJ (US)

(*) Notice: Subject to any disclaimer, the term of this patent is extended or adjusted under 35 U.S.C. 154(b) by 324 days.

(21) Appl. No.: 12/603,372

(22) Filed: Oct. 21, 2009

(65) Prior Publication Data
US 2010/0136594 A1 Jun. 3, 2010

Related U.S. Application Data

(60) Provisional application No. 61/107,046, filed on Oct. 21, 2008.

(51) Int. Cl.
*C12Q 1/37* (2006.01)
*A61K 38/00* (2006.01)

(52) U.S. Cl. .......................................... 435/24; 530/300
(58) Field of Classification Search .................... 435/24; 530/300
See application file for complete search history.

(56) References Cited

U.S. PATENT DOCUMENTS

| 6,864,363 B2* | 3/2005 | Travis et al. .................. 536/23.2 |
| 2007/0037143 A1 | 2/2007 | Jost et al. |
| 2007/0099958 A1* | 5/2007 | Bondebjerg et al. .......... 514/317 |

FOREIGN PATENT DOCUMENTS

| WO | WO 2005/106012 | 11/2005 |
| WO | WO 2007/047995 | 4/2007 |

OTHER PUBLICATIONS

Murakami et al. (Human Prochymase Activation) Journal of Biological Chemistry 270(5)2218-2223.*
McEuen et al. (The conversion of recombinant human mast cell prochymase to enzymatically active chymase by dipeptidyl peptidase I is inhibited by heparin and hhistamine. Eur. J. Biochem (1988) 253, 300-308).*
Adkison et al., "Dipeptidyl Peptidase I Activities Neutrophil-Derived Serine Proteases and Regulates the Development of Acute Experimental Arthritis," *Journal of Clinical Investigation*, 2002; 109(03):363-371.
Bouma et al., "Intracellular Distribution of Cathepsin B and Cathepsin C in Rat Liver," *Biochimica et Biophysica. Acta*, 1966; 113:350-358.
Caughey et al., "New Developments in the Genetics and Activation of Mast Cell Proteases," *Molecular Immunology*, 2001; 38:1353-1357.
Forbes et al., "High-Throughput Mass Spectrometry Screening for Inhibitors of Phosphatidylserine Decarboxylase," *Society for Biomolecular Sciences*, 2007; 12:628-634.
Gelman et al., "Decreased Lysosomal Dipeptidyl Aminopeptidase I Activity in Cultured Human Skin Fibroblasts in Duchenne's Muscular Dystrophy," *J. Clin. Invest.*, 1980; 65:1398-1406.
International Search Report that issued in PCT/US2009/061509, dated Feb. 8, 2010 (4 pages).
Lauritzen et al., "Active Recombinant Rat Dipeptidyl Aminopeptidase I (Cathepsin C) Produced Using the Baculovirus Expression System," *Protein Expression and Purification*, 1998; 14:434-442.
Mcguire et al., "Generation of Active Myeloid and Lymphoid Granule Serine Proteases Requires Processing by the Granule Thiol Protease Dipeptidyl Peptidase I," *The Journal of Biological Chemistry*, 1993; 268:2458-2467.
Mølgaard et al., "The crystal structure of human dipeptidyl peptidase I (cathepsin C) in complex with the inhibitor Gly-Phe-CHN2." *Biochem J.*, 2007; 401: 645-50.
Pham et al., "Dipeptidyl Peptidase I is Required or the Processing and Activation of Granzymes A and B in Vivo," *Proc. Natl. Acad. Sci.*, 1999; 96:8627-8632.
Pham et al., "Papillon-Lefèvre Syndrome: Correlating the Molecular, Cellular, and Clinical Consequences of Cathepsin C/Dipeptidyl Peptidase I Deficiency in Humans," *The Journal of Immunology*, 2004; 173:7277-7281.
Quercia et al., "High-Throughput Screening by Mass Spectrometry: Comparison with the Scintillation Proximity Assay with a Focused-File Screen of AKT1/PKBα," *Journal of Biomolecular Screening*, 2007; 12(4):473-480.
Tran et al., "Dipeptidyl Peptidase I: Importance of Progranzyme Activation Sequences, Other Dipeptide Sequences, and the N-Terminal Amino Group of Synthetic Substrates for Enzyme Activity," *Archives of Biochemistry and Biophysics*, 2002; 403:160-170.
Turk et al., "Structure of Human Dipeptidyl Peptidase I (Cathespin C): Exclusion Domain Added to an Endopeptidase Framework Creates the Machine for Activation of Granular Serine Proteases," *The EMBO Journal*, 2001; 20(23):6570-6582.
Turk et al., "Lysosomal Cysteine Proteases: More than Scavengers," *Biochimica et Biophysica Acta*, 2000; 1477:98-111.
Wolters et al., "Dipeptidyl Peptidase I is Essential for Activation of Mast Cell Chymases, but not Tryptases, in Mice," *The Journal of Biological Chemistry*, 2001; 276:18551-18556.

* cited by examiner

*Primary Examiner* — Karen Cochrane Carlson
*Assistant Examiner* — Natalie Moss
(74) *Attorney, Agent, or Firm* — Toni-Junell Herbert

(57) ABSTRACT

A method of screening a compound which modulates dipeptidyl peptidase I (DPPI) activities comprises the steps of adding a peptide substrate of DPPI to a reaction mixture which comprises DPPI and a compound, wherein the peptide substrate of DPPI has at least 3 amino acids and binds to a binding site of DPPI in addition to the $S_1$-$S_2$ site; and measuring the molecular weight of the substrate, wherein a change in the molecular weight of the substrate is indicative of the presence of DPPI activity.

18 Claims, 2 Drawing Sheets

SEQUENCE LISTING

```
<160> NUMBER OF SEQ ID NOS: 17

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Glu Ile Ile Gly Gly Thr Glu Cys Lys Pro His Ser Arg Pro Tyr
1               5                   10                  15

Met Ala Tyr Leu
            20

<210> SEQ ID NO 2
<211> LENGTH: 20
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 2

Gly Glu Ile Ile Gly Gly Thr Glu Cys Lys Pro His Ser Arg Pro Tyr
1               5                   10                  15

Met Ala Tyr Lys
            20

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Glu Ile Ile Gly Gly
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Glu Ile Ile Gly Gly Thr Glu
1               5

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Glu Ile Ile Gly Gly Thr Glu Cys Lys
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Glu Ile Ile Gly Gly Thr Glu Cys Lys Pro His
1               5                   10

<210> SEQ ID NO 7
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
```

-continued

<223> OTHER INFORMATION: Any amino acid

<400> SEQUENCE: 7

Gly Glu Ile Ile Gly Gly Xaa Glu Ala Lys Pro His Ser Arg Pro Tyr
1               5                   10                  15

Met Val Tyr Leu
            20

<210> SEQ ID NO 8
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ile Ile Gly Gly Thr Glu Cys Lys Pro His Ser Arg Pro Tyr Met Ala
1               5                   10                  15

Tyr Leu

<210> SEQ ID NO 9
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ile Ile Gly Gly Thr Glu Cys Lys Pro His Ser Arg Pro Tyr Met Ala
1               5                   10                  15

Tyr Lys

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ile Ile Gly Gly
1

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ile Ile Gly Gly Thr Glu
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

```
Gly Glu Ile Ile Gly Gly Thr Glu Cys
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ile Ile Gly Gly Thr Glu Cys
1               5

<210> SEQ ID NO 14
<211> LENGTH: 41
<212> TYPE: PRT
<213> ORGANISM: Homo sapiens

<400> SEQUENCE: 14

Met Leu Leu Leu Pro Leu Pro Leu Leu Phe Leu Leu Cys Ser Arg
1               5                   10                  15

Ala Glu Ala Gly Glu Ile Ile Gly Gly Thr Glu Cys Lys Pro His Ser
            20                  25                  30

Arg Pro Met Ala Tyr Leu Glu Ile Val
            35                  40

<210> SEQ ID NO 15
<211> LENGTH: 40
<212> TYPE: PRT
<213> ORGANISM: Homo sapiens

<400> SEQUENCE: 15

Met Gln Pro Leu Leu Leu Leu Ala Phe Leu Leu Pro Thr Gly Ala
1               5                   10                  15

Glu Ala Gly Glu Ile Ile Gly Gly Arg Glu Ser Arg Pro His Ser Arg
            20                  25                  30

Pro Tyr Met Ala Tyr Leu Gln Ile
            35                  40

<210> SEQ ID NO 16
<211> LENGTH: 49
<212> TYPE: PRT
<213> ORGANISM: Homo sapiens

<400> SEQUENCE: 16

Met Thr Leu Gly Arg Arg Leu Ala Cys Leu Phe Leu Ala Cys Val Leu
1               5                   10                  15

Pro Ala Leu Leu Leu Gly Gly Thr Ala Leu Ala Ser Glu Ile Val Gly
            20                  25                  30

Gly Arg Arg Ala Arg Pro His Ala Trp Pro Phe Met Val Ser Leu Gln
            35                  40                  45

Leu

<210> SEQ ID NO 17
<211> LENGTH: 50
<212> TYPE: PRT
<213> ORGANISM: Homo sapiens

<400> SEQUENCE: 17

Met Leu Ser Leu Leu Leu Leu Ala Leu Pro Val Leu Ala Ser Arg Ala
```

-continued

```
1               5                  10                 15
Tyr Ala Ala Pro Ala Pro Val Gln Ala Leu Gln Gln Ala Gly Ile Val
            20                 25                 30

Gly Gly Gln Glu Ala Pro Arg Ser Lys Trp Pro Trp Gln Val Ser Leu
        35                 40                 45

Arg Val
    50
```

HIGH-THROUGHPUT ASSAY FOR EVALUATING DIPEPTIDYL PEPTIDASE I ACTIVITY

CROSS-REFERENCE TO RELATED APPLICATIONS

This application claims benefit to U.S. Provisional Patent Application No. 61/107,046 filed Oct. 21, 2008, the contents of which are incorporated by reference herein in their entirety.

BACKGROUND OF THE INVENTION

1. Field of the Invention

A method is provided for identifying agonists and antagonists of dipeptidyl peptidase I in a high-throughput format. The method uses a peptide substrate that is label-free and binds to multiple substrate binding sites of dipeptidyl peptidase I.

2. Description of the Related Art

Dipeptidyl peptidase I (DPPI) or cathepsin C is a member of the lysosomal papain-type cysteine protease family that also includes cathepsin B, K, H, L, O, and S (Bouma and Gruber, 1996, Biochem. Biophys. Acta 113: 350-358; Turk et al., 2000, Biochem. Biophys. Acta 1477: 98-111). This protease family activates serine proteinases in immune and inflammatory cells.

The physiological role of DPPI is to convert inactive proenzymes into active enzymes by removing two amino acids as a dipeptide unit from the N-terminal end of the proenzymes in immune and inflammatory cells (reviewed by Caughey, G. H., 2002, Molecular Immunology 38: 1353-1357; Wolters et al., 2001, J. Biol. Chem. 276: 18551-18556; McGuire et al., 1993, J. Biol. Chem. 268: 2458-2467; Pham and Ley, 1999, Proc. Natl. Acad. Sci. 96: 8627-8632; Pham et al., 2004, J. Immunol. 173: 7277-7281). DPPI activates many serine proteinases including chymase, tryptase, cathepsin G, elastase, and neutrophil-elastase, granzymes A and B from T-lymphocytes and natural killer cells; and rheumatoid arthritis proteases (Adkison et al., 2002, J. Clin. Invest. 109: 363-371). The enzymes or serine proteases activated by DPPI are needed for defense responses. In addition, the unregulated DPPI has been shown to cause over-activation of proteases associated with diseases including chronic obstructive pulmonary disease, Papillon-Lefevre Syndrome, Sepsis, arthritis and other inflammatory disorders. Therefore, DPPI is a potential target for therapeutic treatment.

It is proposed that DPPI consists of four identical monomers. Each monomer is produced from a precursor polypeptide, which is cleaved into a N-terminal exclusion domain, an activation peptide, and a papain-like domain. The papain-like domain is further cleaved into a heavy chain and a light chain. Subsequently, the N-terminal exclusion domain, the heavy and the light chains fold into a monomer, which tetramizes into the mature DPPI of about 200 kDa (Turk et al., 2001 EMBO J., 20: 6570-6582).

Recent crystallization of DPPI identified some structures, including an active site cleft and substrate binding sites, involved in the dipeptidyl proteolytic activity. The substrate binding sites reside on the external part of the papain-like structure and form hydrogen bonds with the substrates. The site that binds to the first amino acid at the N-terminal side of the cleaved bond of the substrate is referred to as the $S_1$ binding site, the site that binds to the second amino acid at the N-terminal side is referred to as the $S_2$ binding site. Further, the site that binds to the first amino acid at the C-terminal side of the cleaved bond of the substrate is referred to as the $S_1'$ binding site, and the site that binds to the second amino acid at the C-terminal side is referred to as the $S_2'$ binding site, etc (Turk et al., 2001, EMBO J., 20:6570-6582; Molgaard et al., 2007, Biochem. J., 401:645-650). The corresponding site in a DPPI substrate is referred to as $P_1, P_2, P_1', P_2'$ etc, where $P_1$ of the substrate binds to the $S_1$ site of DPPI, $P_2$ of the substrate binds to $S_2$ of DPPI, and $P_1'$ of the substrate binds to the $S_1'$ site of DPPI, etc. Based on the crystallographic results of a binding complex of DPPI and a substrate of 6 amino acids, Molgaard et al. proposes a model where DPPI contains the $S_2$-$S_1$ and $S_1'$-$S_4'$ substrate binding sites. Since DPPI binds to larger substrates such as human prochymase of 228 amino acids in vivo; the substrate binding sites of DPPI may contain more than $S_2$-$S_1$-$S_1'$-$S_4'$, even to $S_2$-$S_1$-$S_1'$-$S_{18}'$.

As DPPI is a potential therapeutic target, several assays for analyzing DPPI activity have been commonly used (Gelman et al., J. Clin. Invest. 1980, 65: 1398-1406; (Tran et al., Arch. Biochem. Biophys. 2002, 403: 160-170). Gelman et al. uses a labeled dipeptide of Gly-Phe-β-naphthylamide as substrate and determined DPPI activity by measuring the concentration of free β-naphthylamide with a spectrophotofluorometer. Similarly, Tran et al. uses several dipeptides labeled with 7-amino-4-methylcoumarin as DPPI substrates and determined DPPI activity by measuring the concentration of free methylcoumarin with a spectrophotofluorometer. Tran et al. shows that the dipeptide substrate of Ala-Hph-7-amino-4-methylcoumarin is the best substrate for DPPI, even though the substrate contains a non-physiological residue Hph (homophenylalanine).

These commonly used dipeptide substrates with fluorescence labels have several problems. First, the dipeptide substrate only binds to the $S_1$ and $S_2$ sites. This is partial or incomplete in comparison to biological substrates in vivo which binds to a binding site in addition to the $S_1$ and $S_2$ sites. The incomplete or partial binding may be non-specific and hence lead to the identification of false positive or negative compounds. Also, the additional step of fluorescence detection is needed to detect the DPPI activity. This additional step makes the assay difficult to be adapted for use in a high-throughput format.

Therefore, there is still a need to develop an assay that uses a substrate which is label-free and biologically related for analyzing DPPI activity. Also, there is a need to develop a DPPI assay suitable for use in a high-throughput format to enable efficient screening of a large number of compounds or agents for drug development.

The label-free technology has been combined with a mass spectrometry system to analyze enzymatic reactions. Quercia et al. (J. Biomol. Screen. 12: 473-480, 2007) identifies the kinase AKT1/PKBα inhibitors using mass spectrometry in multiple reaction monitoring. Similarly, Forbes et al. (J. Biomol. Screen. 11: 628-634, 2007) evaluates phosphortidylserine decarboxylase in 96-well plates using mass spectrometry in multiple reaction monitoring. A mass spectrometry detection system in a high-throughput format has not been applied for analyzing DPPI activity.

The present application provides a method for assaying DPPI activity. The method utilizes a label-free peptide substrate that comprises biologically related amino acid sequences and binding specificity. The assay may be detected using a mass spectrometry system and may be operated in a high-throughput format, which reduces processing time and increases throughput which are desired for screening compounds. The method is also useful for differential tracking of fragment-based compounds for drug development and evaluating other dipeptidyl proteolytic reactions for functional studies.

SUMMARY

An object of the present application is to provide a method for screening compounds which modulate DPPI activities. The method comprises the steps of adding a substrate of DPPI to a reaction mixture which comprises DPPI and the compounds, wherein the substrate has 3 to 100 amino acids and binds to a binding site of DPPI in addition to the $S_1$-$S_2$ site, and measuring a change in the molecular weight of the substrate and/or a change in the mass ratio of the substrate and products, wherein the change in molecular weight of the substrate or mass ratio is indicative of the presence of DPPI activity.

According to one embodiment of the present invention, the compound may be 2-(piperidin-1-ylcarbonyl)phenol or 2-(piperidin-1-ylcarbonyl)aniline.

Another object is to provide label-free DPPI substrates useful for screening compounds which modulate DPPI activity. Exemplary DPPI substrates may be selected from the group consisting of SEQ ID NOs: 1-7. The DPPI substrate may preferably comprise a peptide having 20 amino acids. The DPPI substrate is preferably label-free.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

DETAILED DESCRIPTION OF THE PRESENTLY PREFERRED EMBODIMENTS

Figure 1A:
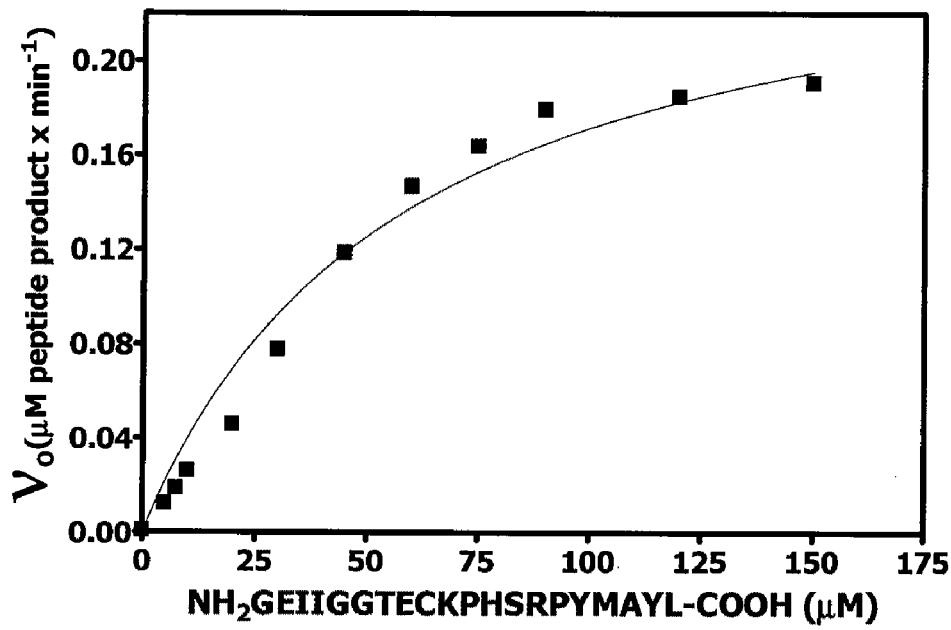
FIG. 1. Initial velocity analysis for DPP1 kinetic constant in reaction with a 20-mer substrate (A) and a dipeptide substrate (B). (A) About 2 nM of DPPI was used in the reaction with the 20-mer substrate of GEIIGGTECKPHSRPYMAYL (SEQ ID NO:1) and the reaction was monitored using a mass spectrometry system. (B) About 0.4 nM of DPP1 was used in the reaction with the dipeptide substrate of GR-α-methylcoumarin and the reaction was monitored using a rate-based format monitoring fluorescence at $E_M$=460 nm and $E_X$=380 nm. Initial rates are taken from kinetic data where less than 7% substrate turnover was achieved.

To detect the activity of dipeptidyl peptidase I (DPPI) in the presence of an agonist or an antagonist of DPPI, a peptide which is used as a substrate of DPPI, is added into a reaction mixture such that the reaction mixture contains a reaction buffer, an agonist or an antagonist of DPPI, DPPI and a substrate. A buffer system of PIPES, HEPES, sodium phosphate or any buffering system where the pKa is about 7.0 can be used for the DPPI assay. A HEPES buffer system is preferred. For example, a 10× reaction buffer is 500 mM HEPES at pH 7.0, 1 M NaCl, and 0.05% Tween-20. Other buffer systems commonly known to a person skilled in the art may also be used. Prior to the reaction, DTT or glutathione is added to the 1× reaction buffer to a final concentration of 2 mM.

DPPI may be obtained from a commercial source, produced by recombinant DNA technology, or isolated or purified from cells by methods commonly known to a person skilled in the art.

Any peptides of at least 3 amino acids, preferably 5 to 100 amino acids and most preferably 10 to 50 amino acids that binds to more than the $S_1$-$S_2$ substrate binding site of DPPI may be used as a substrate for detecting the proteolytic activity of DPPI. The number of the substrate binding sites of the peptide substrate may be 3 to 100, preferably 5 to 50 and most preferably 6 to 20. Therefore, the peptide substrate binds to DPPI at the $S_1$-$S_2$ substrate binding site and at least one additional substrate binding site of $S_1'$-$S_{98}'$, preferably $S_1'$-$S_{48}'$ and most preferably $S_1'$-$S_4'$.

The peptide substrate of the present application is not labeled or modified with any flurogenic or chromogenic agents. The peptide substrate may be synthesized chemically, expressed using recombinant DNA technology, or isolated or purified from cells by methods commonly known to a person skilled in the art.

As used herein, the term polypeptide refers to three or more amino acids joined to each other by peptide bonds or modified peptide bonds, i.e. peptide isosteres. Polypeptide refers to both short chains, commonly referred to as peptides, oligopeptides or oligomers, and to longer chains, generally referred to as proteins. Polypeptides may contain amino acids other than the 20 naturally occurring amino acids. Polypeptides include amino acid sequences modified either by natural processes, such as post-translational processing, or by chemical modification techniques that are well known in the art. Such modifications are well described in research literature. Modifications may occur anywhere in a polypeptide, including the peptide backbone, the amino acid side-chains and the amino or carboxyl termini.

A reaction volume of 5-50 μls, preferably 10 or 20 μls, is aliquoted into a tube or a plate commonly used in the laboratory and assayed for DDPI activity by measuring the substrate turnover. As used herein, the substrate turnover refers to the reduction in the quantity of substrate and the subsequent increase in the quantity of product. The substrate turnover may be measured by monitoring the molecular mass of the substrate and the product. A mass spectrometry system is preferred. By way of example, the concentrations of substrates and products can be determined by single ion monitoring (SIM) technology using the Agilent MSD with Agilent Chemstation software or the like known to a person of ordinary skill in the art. Data was analyzed using Agilent Chemstation and BioTrove Rapidfire Integrator. The assay was designed to tolerate less than 10% substrate turnover for compound testing.

An equilibrium of a general enzymatic reaction is illustrated below:

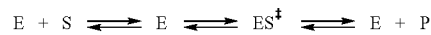

wherein E is an enzyme, S is a substrate for the enzyme and P is the product of the reaction.

The equilibrium is modified to illustrate the dipeptidyl proteolysis reaction in the DPPI assay with a peptide substrate of the present application:

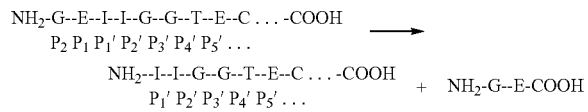

When initiated, DPPI cleaves and removes two amino acids G-E or Gly-Glu from the N-terminus of the peptide substrate having 20 amino acids, G-E-I-I-G-G-T-E-C-K-P-H-S-R-P-Y-M-A-Y-L (SEQ ID NO:1). This results in a change of molecular weight or mass of the peptide substrate from 2,224 Da to 2,037 with a difference of 187 Da. The molecular weight or mass of the peptide substrate in the reaction may be detected by a mass spectrometry using single ion monitoring. The change or difference of the peptide substrate detected by SIM is from 1,112 amu (atomic mass unit) to 1,018.5 amu. This may be used to determine the value for the substrate turnover.

Once the rate of the substrate turnover under the initial velocity condition, the kinetic constants for DPPI and the peptide substrate are calculated using the following formula (I):

$$Y = V_{MAX}((X+Et+K_M) - ((((Et+X+K_M)^2) - (4XEt))^{0.5}))/(2Et)$$

wherein
Y is concentration of substrate turnover
X is substrate concentration
Et is DPPI concentration
$K_M$ is substrate concentration at ½ $V_{MAX}$
$V_{MAX}$ is substrate turnover at substrate saturation For screening test compounds which modulate DPPI activity, the inhibition of DPPI activity may be calculated using the following formula:
Quantity of Substrate Turnover in a Positive Control:

$$[S] \times \left( \frac{(SIM_{PC} - SIM_{NC})}{(SIM_{SPC} - SIM_{SNC}) + (SIM_{PC} - SIM_{NC})} \right)$$

Quantity of Substrate Turnover in a Sample Containing a Test Compound:

$$[S] \times \left( \frac{(SIM_P - SIM_{NC})}{(SIM_S + (SIM_P - SIM_{NC}))} \right)$$

Percent inhibition=

$$\left( 1 - \left( \frac{\left(\frac{(SIM_P - SIM_{NC})}{(SIM_S + (SIM_P - SIM_{NC}))}\right) \times}{\left(\frac{(SIM_{PC} - SIM_{NC})}{(SIM_{SPC} + (SIM_{PC} - SIM_{NC}))}\right)^{-1}} \right) \right) \times 100$$

OR $$\left( 1 - \left( \frac{(\mu M \text{ substrate turnover of sample}) \times}{(\mu M \text{ substrate turnover of pos. control})^{-1}} \right) \right) \times 100$$

wherein
[S] is concentration of the substrate (μM)
$SIM_S$ is SIM of the substrate in sample (area under curve from amu)
$SIM_{SPC}$ is SIM of the substrate in positive control samples (area under curve from amu)
$SIM_P$ is SIM of the product in sample (area under curve from amu)
$SIM_{PC}$ is SIM of product for positive control (area under curve from amu)
$SIM_{SPC}$ is SIM of the substrate in positive control samples (area under curve from amu)
$SIM_{NC}$ is SIM of product for negative control (area under curve from amu)
$SIM_{SNC}$ is SIM of substrate for negative control (area under curve from amu)
wherein a positive control is a reaction without any test compound, a negative control is a reaction without DPPI or substrate, a sample is a reaction containing a test compound.

When a candidate compound is identified, the $IC_{50}$ of the DPPI inhibition by the candidate compound is calculated using the formula (II):

$$S_i = S_o + \frac{(S_{min} - S_o)[I]^h}{IC_{50}^h + [I]^h}$$

wherein
$S_i$ is net substrate turnover signal of sample
$S_o$ is net substrate turnover signal of positive control
$S_{min}$ is net am signal of negative control
I is concentration of a candidate compound
wherein a positive control is a reaction without any test compound and a negative control is a reaction without DPPI or substrate.

The above described assay may be used in a high-throughput format for screening test compounds, and identifying candidate compounds which modulate the activities of DPPI. In such case, the reaction mixture is first aliquoted to microtiter plates containing a plurality of wells such as 96- or 386-well plates, then the plates are loaded to a detection system such as a mass spectrometry or the like, which reads the reaction in each well of each plate to generate numeric data.

Thus, while there have been shown and described and pointed out fundamental novel features of the invention as applied to a preferred embodiment thereof, it will be understood that various omissions and substitutions and changes in the form and details of the compounds, methods and devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

EXAMPLE 1

Preparation of A 10× HEPES Buffer System and Dipeptidyl Proteinase I

A 10× reaction buffer of 500 mM HEPES at pH 7.0, 1 M NaCl, and 0.05% Tween-20 was prepared. Prior to the reaction, DTT or other suitable reducing agent was added to 1× reaction buffer of 50 mM HEPES at pH 7, 100 mM NaCl and 0.005% Tween-20 to a final concentration of 2 mM. A reaction volume of 10 or 20 μls was aliquoted into a 384-well polypropylene plate for the DDP-1 activity.

DPPI was over-expressed and purified using a bacculovirus system in Hi5 insect cells according to Lauritzen et al. (1998, Protein Expr. Purif 14, 434-442), the content of which is incorporated herein by reference in its entirety. The recombinant baculovirus encoding a DPPI precursor was prepared according to the instructions of the Baculovirus Expression System (Invitrogen, Carlsbad, Calif.). Briefly, recombinant baculovirus containing cDNA of human and mouse DDP precursors were transfected into the Hi5 insect cells. After about 4-5 days post transfection, the media was harvested and DPPI precursor was purified using a butyl-Sepharose (GE Healthcare) chromatography at pH 4.5. The DPP1-containing fractions were pooled and dialyzed for two days at pH 7.0 to complete activation. During secretion and activation, the signal sequence and the activation peptide were cleaved off and resulted in a fully activated enzyme. The dialyzed heterotrimeric and active DPP1 was further purified on Q-Sepharose (GE Healthcare), concentrated by ultrafiltration (Amicon, Ultra-15, 10000 MWCO, Millipore), and dialyzed in a final buffer of 20 mM Bis-Tris/HCl, pH 7.0, 0.1 M NaCl, 2 mM DTT, and 2 mM EDTA. All purification and dialysis steps were carried out at 4° C. DPP1 was aliquoted, flash-frozen in liquid nitrogen, and stored at −80 ° C. Correct N-termini for three chains were confirmed by N-terminal sequencing.

EXAMPLE 2

Design of Peptide Substrates Which Binds to Multiple Substrate Binding Site of DPPI The N-terminus peptide sequences of human chymase, cathepsin G, elastase, and tryptase were aligned as below.

```
Chymase      ---------MLLLPLPLLLFLLCSRAEAGEIIGGTECKPHSRPMAYLEIV

Cathpsin G   ----------MQPLLLLLAFLLPTGAEAGEIIGGRESRPHSRPYMAYLQI

Elastase     -MTLGRRLACLFLACVLPALLLGGTALASEIVGGRRARPHAWPFMVSLQL

Tryptase     MLSLLLLALPVLASRAYAAPAPVQALQQAGIVGGQEAPRSKWPWQVSLRV

Consensus              AEAGEIIGG EAKPHSRPYMVYL
```

The peptides of GEIIGGTECKPHSRPYMAYL (SEQ ID NO: 1), NH$_2$-GEIIGGTECKPHSRPYMAYK-COOH (SEQ ID NO: 2), NH$_2$-GEIIGG-COOH (SEQ ID NO: 3), and NH$_2$-GEIIGGTE-COOH (SEQ ID NO: 4) were selected as DPPI substrates. The substrates and the corresponding product peptides of NH$_2$-IIGGTECKPHSRPYMAYL-COOH (SEQ ID NO: 8), NH$_2$-IIGGTECKPHSRPYMAYK-COOH (SEQ ID NO: 9), NH$_2$-IIGG-COOH (SEQ ID NO: 10), and NH$_2$-IIGGTE-COOH (SEQ ID NO: 11) were synthesized (AnaSpec, San Jose, Calif.) and dissolved in Milli-Q water. The single ion monitoring (SEM) for the peptide substrates and their products were described in Table 1.

A skilled person in the art will recognize that other peptide sequences can be used as substrates according to the method described herein, for example NH$_2$-GEIIGGTECK-COOH (SEQ ID NO: 5), NH$_2$-GEIIGGTECKPH-COOH (SEQ ID NO: 6), and a peptide of NH$_2$-GEIIGGXEAKPHSRPYMV-YL-COOH (SEQ ID NO: 7) where X is any native or modified amino acid.

EXAMPLE 3

DPPI Assays with the Peptide Substrates

A standard curve for the 20-mer substrate peptide of NH2-GEIIGGTECKPHSRPY-MAYL-COOH (SEQ ID NO: 1) and the 18-mer product peptide (NH2-IIGGTECKPHSRPY-MAYL-COOH (SEQ ID NO: 8) was generated by a mass spectrometry system using single-ion monitoring detection.

About 2 nM of DPPI was incubated with about 0.5, 1, 2, 4, 8, 16, 32, 64, 90, 128, 150 μM of the 20-mer substrate in the reaction buffer of 50 mM HEPES (pH 7.0), 100 mM NaCl, 0.005% Tween-20, and 2 mM of DTT or GSH. The reaction was incubated at about 27° C. and terminated with about 1/10 volume of 2% trifluoroacetic acid at multiple time points at 0, 2, 5, 10, 20, 30, 45, 60, 75, 90, and 120 mins. An aliquot of about 10 μl of the quenched reaction was used for detecting the substrate turnover by RapidFire (BioTrove, Woburn, Mass.) with a C$_4$ cartridge. The reaction was loaded onto the cartridge, which was equilibrated with the stationary phase of 0.1% formic acid+0.02% TFA and developed with the mobile phase of 90% MeCN+0.1% formic acid+0.02% TFA at about 1 ml per min. The 20-mer substrate at SIM 1112 amu (atomic mass unit) and the corresponding 18-mer product at SIM 1019 were monitored using Agilent 1100 series LCMSD (Santa Clara, Calif.) in the positive ion mode monitoring.

Figure 1B:
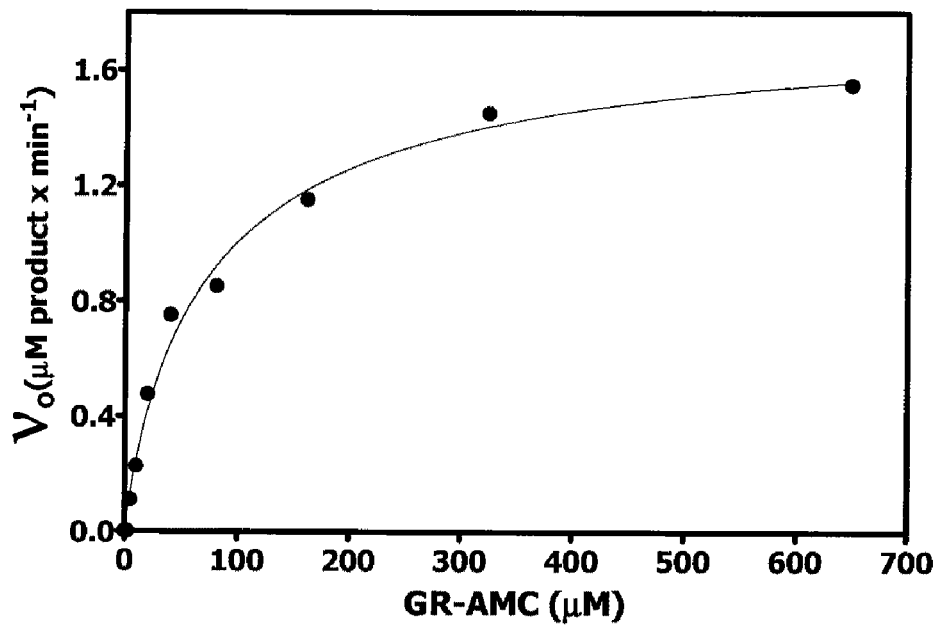

Initial reaction rates were taken from kinetic data where less than 7% substrate turnover was achieved. The results, as shown in FIG. 1, indicated that the substrate turnover may be represented as a hyperbolic curve. The value for $K_M$, $K_{cat}$, and second order rate constant were calculated to be about 62 μM, 69 Mmin$^{-1}$, and 1.95×10$^4$ M$^{-1}$sec$^{-1}$, respectively (Table 2). These values were set up conditions for evaluating test compounds in the DPPI assay.

TABLE 1

SIM of substrate and product peptides.

| SEQ ID | Peptide Substrate | SIM | SEQ ID | Corresponding Product of Peptide Substrate | SIM |
|---|---|---|---|---|---|
| 1 | GEIIGGTECKPHSRPYMAYL | 1111.8 | 8 | IIGGTECKPHSRPYMAYL | 1018.8 |
| 2 | GEIIGGTECKPHSRPYMAYK | 746.2 | 9 | IIGGTECKPHSRPYMAYK | 684.1 |
| 3 | GEIIGG | 544.6 | 10 | IIGG | 358.5 |
| 4 | GEIIGGTE | 774.8 | 11 | IIGGTE | 588.7 |

EXAMPLE 4

Rate-Based DPPI Assays Using the Dipeptide and the Peptide Substrates

The DPPI activity was analyzed with either the dipeptide substrate, Gly-Arg, labeled with alpha-methylcoumarin (AMC), or the 20-mer peptide substrate of SEQ ID NO: 1. For the dipeptide substrate, about 0.4 nM of DPPI was incubated with about 1, 2, 5, 10, 25, 50, 100, 150, 300, 600 µM of the dipeptide substrate in 10 ul of reaction buffer of 50 mM Hepes (pH 7.0), 100 mM NaCl, 0.005% Tween-20, and 2 mM of DTT or GSH. The fluorescence ($E_x$=380 nm, $E_M$=460 nm) was monitored continuously from about 0 to 10 mins, using a Safire II (Tecan, Switzerland) to determine the DPPI activity. The condition for the 20-mer peptide substrate was the same as described above.

The kinetic constant of the DPPI assay with either substrate was shown in Table 2. The values of both $k_{cat}$ and $2^{nd}$ order rate constant of the reaction containing the 20-mer substrate peptide were reduced compared to those of reaction containing the labeled dipeptide. The results show that the 20-mer substrate has a different kinetic mechanism, which is likely due to the product dissociation being the rate-limiting step. The products of the reaction with the 20-mer substrate include a N-terminal 2-mer peptide and a C-terminal 18-mer peptide. The 18-mer product peptide binds to the DPPI binding sites which cannot be examined using the dipeptide substrate. This suggests that the DPPI assay using the dipeptide substrate may not provide sufficient information on the efficacy of the tested compounds.

TABLE 2

Summary of kinetic constants of DPPI assay with the 20-mer substrate of GEIIGGTECKPHSRPYMAYL and the dipeptide substrate of GR.

|  | $K_M$ (µM) | $k_{cat}$ (Mmin$^{-1}$) | $2^{nd}$ order rate constant (M$^{-1}$sec$^{-1}$) |
|---|---|---|---|
| 20-mer | 62 | 69 | $1.95 \times 10^4$ |
| Dipeptide | 64 | 5667 | $1.48 \times 10^6$ |

EXAMPLE 5

Screening Test Compounds that Modulate DPPI Activities

Two fragment compounds, 2-(piperidin-1-ylcarbonyl)phenol and 2-(piperidin-1-ylcarbonyl)aniline were evaluated for their activity to modulate DPPI. A dilution series of the compounds of about 0.1 mM to about 100 mM was made in 100% DMSO. About one µl of a test compound and about 8 µl of about 3.75 nM DDP-1 were added to a 384-well polypropylene plate (Greiner Bio-One North America Inc., Monroe, N.C.). The proteolytic reaction was initiated by the addition of about 1 µl of 200 µM substrate. The reaction was incubated at 27° C. for 60 min and terminated with an addition of about 25 µl of 0.1% formic acid+0.02% TFA. An aliquot of about 10 µl of the quenched reaction was analyzed by RapidFire™ as described in Examples 3 and 4.

Figure 2A:
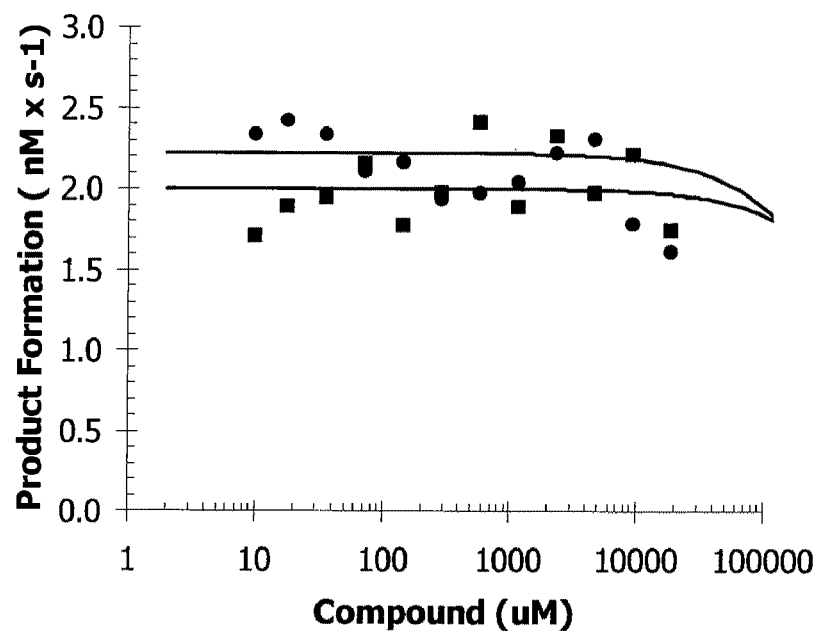
FIG. 2. Evaluating the DPPI-modulating activity with two test compounds using a dipeptide substrate (A) and using a 20-mer peptide substrate (B). (A) About 0.4 nM of DPP1 and about 10 μM of dipeptide substrate GR-α-methylcoumarin were used in a rate-based format and monitored with fluorescence at $E_M$=460 nm and $E_X$=380 nm. (B) About 2 nM of DPPI and 20 μM of the 20-mer peptide substrate GEIIG-GTECKPHSRPYMAYL (SEQ ID NO:1) were used in a reaction and monitored with a mass spectrometry system. 2-(piperidin-1-ylcarbonyl)phenol is represented by solid squares and 2-(piperidin-1-ylcarbonyl)aniline is represented by solid circles. $R^2$-values is >0.95.
Figure 2B:
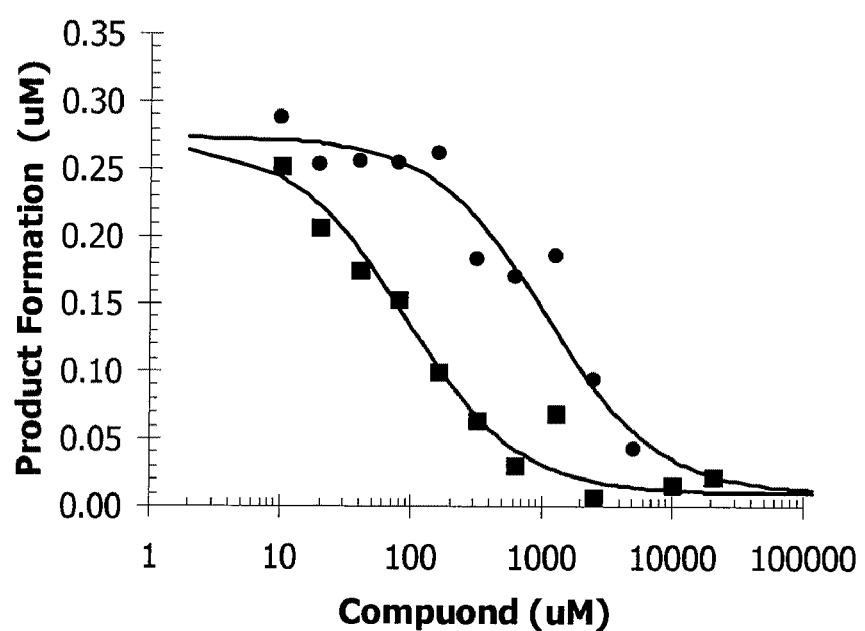

The results of Experiment 5 were summarized in FIG. 2. In the reaction with the dipeptide substrate, neither compound, even in high concentration of 10 mM, affected the DPPI activity. However, in the reaction with the 20-mer substrate, both compounds modulated the DPPI activity in a concentration dependent manner. The semi-log plot analysis showed that the $IC_{50}$-values for the 2-(piperidin-1-ylcarbonyl)phenol and 2-(piperidin-1-ylcarbonyl)aniline were about 0.1 mM and about 1 mM, respectively. Previously, these compounds have not been shown to modulate DPPI activity.

The present application provides a method for assaying DPPI activity preferably using a label-free peptide as DPPI substrate. The method has several advantages compared to the labeled dipeptide substrate that is commonly used. For example, the label-free substrate provides a direct detection of unmodified compounds and eliminates the limitations due to labeling and secondary detection system. Also, the label-free substrate is easily adapted for a high-throughput format. In addition, the peptide substrate has similar binding specificity to DPPI active site as those of physiological targets in cells. Further, the increased binding specificity allows for evaluating or identifying compounds that bind outside of the $S_1$-$S_2$ region of the active site. The compounds bind to active sites in addition to $S_1$-$S_2$, such as $S_1'$ to $S_4'$, increases logarithmically and specificity.

---

We claim:

1. A method of screening compounds to identify compounds which modulate dipeptidyl peptidase I (DPPI) activities, comprising the steps of:
   a. adding a substrate peptide of DPPI to a reaction mixture which comprises DPPI and a compound to be tested, wherein said substrate of DPPI is selected from the group consisting of:
      (i) an isolated peptide of SEQ ID NO: 1;
      (ii) an isolated peptide of SEQ ID NO: 2;
      (iii) an isolated peptide of SEQ ID NO: 3;
      (iv) an isolated peptide of SEQ ID NO: 4;
      (v) an isolated peptide of SEQ ID NO: 5;
      (vi) an isolated peptide of SEQ ID NO: 6;
      (vii) an isolated peptide of SEQ ID NO: 7; and
      (viii) an isolated peptide of up to 100 amino acids comprising SEQ ID NO:1, SEQ ID NO:2 or SEQ ID NO: 7;
   b. measuring the molecular weight of said substrate and/or mass ratio of said substrate peptide and corresponding product peptide;
   c. comparing the results of step (b) to the results of a positive control containing no test compound;
   d. determining whether the molecular weight and/or mass ratio differs from the control; and
   e. selecting a compound for which the results differ from the control.

2. The method of claim 1, wherein said substrate is label-free.

3. The method of claim 1, wherein said substrate is up to about 50 amino acids long.

4. The method of claim 1, wherein said substrate is an isolated peptide selected from the group consisting of SEQ ID NOs: 1-7.

5. The method of claim 1, wherein said substrate is an isolated peptide of SEQ ID NO: 1.

6. The method of claim 1, wherein said compound is 2-(piperidin-1-ylcarbonyl)phenol.

7. The method of claim 1, wherein said compound is 2-(piperidin-1-ylcarbonyl)aniline.

8. A DPPI substrate selected from the group consisting of an isolated peptide of SEQ ID NOs: 1-7.

9. The DPPI substrate of claim 8, wherein said substrate is the isolated peptide of SEQ ID NO: 1.

10. A method of screening compounds to identify compounds which modulate dipeptidyl peptidase I (DPPI) activities, comprising the steps of:
    a. adding a substrate peptide of DPPI to a positive control mixture which comprises DPPI and lacks a compound to be tested, wherein said substrate of DPPI is selected from the group consisting of:
       (i) an isolated peptide of SEQ ID NO: 1;
       (ii) an isolated peptide of SEQ ID NO: 2;
       (iii) an isolated peptide of SEQ ID NO: 3;
       (iv) an isolated peptide of SEQ ID NO: 4;
       (v) an isolated peptide of SEQ ID NO: 5;
       (vi) an isolated peptide of SEQ ID NO: 6;
       (vii) an isolated peptide of SEQ ID NO: 7; and
       (viii) an isolated peptide of up to 100 amino acids comprising SEQ ID NO:1, SEQ ID NO:2 or SEQ ID NO: 7;
    b. measuring the molecular weight of said substrate peptide and/or mass ratio of said substrate peptide and corresponding product peptide in the control mixture;
    c. adding the substrate peptide of DPPI to a reaction mixture which comprises DPPI and the compound to be tested;
    d. measuring the molecular weight of said substrate peptide and/or mass ratio of said substrate peptide and corresponding product peptide in the reaction mixture;
    e. comparing the results of step b) and d) to determine whether the molecular weight and/or mass ratio differs, wherein a difference is indicative of a compound that modulates DPPI activities; and
    f. selecting those compounds which modulate DPPI activity.

11. The method of claim 10, wherein said substrate is label-free.

12. The method of claim 10, wherein said substrate is up to about 50 amino acids long.

13. The method of claim 10, wherein said substrate is an isolated peptide selected from the group consisting of SEQ ID NOs: 1-7.

14. The method of claim 10, wherein said substrate is an isolated peptide of SEQ ID NO: 1.

15. The method of claim 1, wherein the compounds selected are those that increase the activity of DPPI.

16. The method of claim 1, wherein the compounds selected are those that decrease the activity of DPPI.

17. The method of claim 10, wherein the compounds selected are those that increase the activity of DPPI.

18. The method of claim 10, wherein the compounds selected are those that decrease the activity of DPPI.

* * * * *